US00PP17657P2

(12) United States Plant Patent
Gotou

(10) Patent No.: US PP17,657 P2
(45) Date of Patent: Apr. 24, 2007

(54) POINSETTIA PLANT NAMED 'CAROUSEL DARK RED'

(50) Latin Name: *Euphorbia pulcherrima*
Varietal Denomination: Carousel Dark Red

(75) Inventor: Shoji Gotou, Kounan (JP)

(73) Assignee: Fischer Horticulture LLC, Boulder, CO (US)

( * ) Notice: Subject to any disclaimer, the term of this patent is extended or adjusted under 35 U.S.C. 154(b) by 2 days.

(21) Appl. No.: 11/358,012

(22) Filed: Feb. 21, 2006

(51) Int. Cl.
*A01H 5/00* (2006.01)

(52) U.S. Cl. ..... Plt./307; Plt./302

(58) Field of Classification Search ..... Plt./302, Plt./307
See application file for complete search history.

(56) References Cited

U.S. PATENT DOCUMENTS

PP14,630 P2 * 3/2004 Voogt ..... Plt./306

* cited by examiner

*Primary Examiner*—Anne Marie Grunberg
*Assistant Examiner*—S. B. McCormick-Ewoldt
(74) *Attorney, Agent, or Firm*—Jondle & Associates, P.C.

(57) ABSTRACT

A new poinsettia plant particularly distinguished by relatively short, deep-red bracts with curled margins forming a rosette-like inflorescence, deep-green foliage with ovate leaves and weak lobes, upright directed branches and a mid-season flowering response is disclosed.

1 Drawing Sheet

Genus and species: *Euphorbia pulcherrima* (Willd. Ex Klotzsch).
Variety denomination: 'Carousel Dark Red'.

BACKGROUND OF THE NEW PLANT

The present invention comprises a new and distinct cultivar of poinsettia plant, botanically known as *Euphorbia pulcherrima* (Willd. Ex Klotzsch) and hereinafter referred to by the cultivar name 'Carousel Dark Red'. The new cultivar is the result of a naturally occurring whole young plant mutation in the bright-red poinsettia plant 'Future' (U.S. application Ser. No. 09/590,012—abandoned) discovered in July 2003 in a greenhouse in Kounan-shi, Aichi prefecture, Japan.

The new cultivar has been asexually reproduced repeatedly by vegetative cuttings in Japan starting in July 2004. The resulting plants were used for trail cultivation and evaluation as flowering plants in December 2004. The clone proved to be stable and uniform. 'Carousel Dark Red' has not been observed under all possible environmental conditions. The present invention has been found to retain its distinctive characteristics through successive asexual propagations.

Plant Breeder's Rights for this cultivar were applied for in Japan on Feb. 3, 2006.

SUMMARY OF THE INVENTION

The following are the most outstanding and distinguishing characteristics of this new cultivar when grown under normal horticultural practices in Japan and Hillscheid, Germany.

1. A deep-red bract color;
2. Relatively short bracts with curled margins, forming a rosette-like inflorescence;
3. Deep-green foliage and ovate leaves with weak lobes;
4. Upright-directed branches; and
5. A mid-season flowering response.

DESCRIPTION OF PHOTOGRAPH

This new poinsettia plant is illustrated by the accompanying photograph which shows overall plant habit including blooms, buds, and foliage of the plant; the colors shown are as true as can be reasonably obtained by conventional photographic procedures. The photograph is of a whole plant about 18-weeks old and in full flower, grown in a greenhouse in Hillscheid, Germany, in early December of 2005.

DESCRIPTION OF THE NEW CULTIVAR

The following detailed description sets forth the distinctive characteristics of 'Carousel Dark Red'. The data which define these characteristics were collected from asexual reproductions carried out in Hillscheid, Germany. The plant history was taken on 18-week old plants which were planted as rooted cuttings in 14-cm pots on Aug. 1, 2005 and were pinched 14 days later, with 7 to 8 leaves remaining. The plants were grown in a greenhouse at a minimum temperature of 18° C. and a ventilation temperature of 24° C. The plants initiated flowers under natural short-day conditions of Fall. No black cloth was applied to the greenhouse to simulate short-day conditions and growth regulator was not applied to the plants. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Euphorbiaceae.
*Botanical.*—*Euphorbia pulcherrima* (Willd. Ex Klotzsch).
*Common name.*—Poinsettia.

Parentage: Mutation of the bright-red poinsettia plant 'Future' (U.S. application Ser. No. 09/590,012 — abandoned).

Growth:

*Form.*—Shrub, self-branching.

*Growth and branching habit.*—Medium sized and fairly compact; pinched plants are bushy with the braches directed upright at an angle of 60°.

*Height* (*from soil line to the top*).—26.6 cm.

*Width.*—34.0 cm.

*Time to produce a finished flowering plant.*—About 17 weeks (the total cultivation time) for a 14-cm pot or about 9 weeks after the autumnal equinox (early December) when marketable quality is reached.

*Time to initiate and develop roots.*—20 to 24 days in a greenhouse at 22° C. to 24° C.

Branches:

*Average number.*—6.2.

*Length of branches.*—16 cm to 18 cm.

*Internode length.*—1.2 cm to 2.5 cm.

*Diameter of branches.*—0.6 cm.

*Stem color.*—Upper part: Mainly RHS 183B (purple-brown). Lower part: RHS 146B. Base color: RHS 146B. Shoot tip: RHS 144A (yellowish-green).

Leaves:

*Quantity.*—30 leaves per plant (4 to 6 leaves per branch).

*Arrangement.*—Alternate.

*Size.*—Length: 11 cm to 13 cm. Width: 7 cm to 8 cm.

*Shape.*—Ovate, relatively narrow and occasionally weakly twisting.

*Margin.*—Entire.

*Apex.*—Acuminate.

*Base.*—Truncate to obtuse.

*Lobes.*—Few, weak to medium degree, rounded or pointed.

*Color* (*mature leaves*).—Upper surface: Near RHS 139A (dark-green). Lower surface: RHS 137A (green).

*Color* (*immature leaves*).—Upper surface: RHS 137A. Lower surface: RHS 137C.

*Texture.*—Upper surface: Smooth, only weakly veined. Lower surface: Smooth, except for the slightly protruding midrib and finer side veins in a pinnate pattern.

*Venation color.*—Upper surface: RHS 185A (reddish), most distinct at the base of the leaves. Lower surface: RHS 145B (pale-green).

*Variegation.*—None.

*Leaf petiole.*—Length: 2 cm to 4 cm. Diameter: 0.3 cm. Color: Upper surface: RHS 53A (deep-red). Lower surface: RHS 174B (brown-orange). Texture: Glabrous.

*Aspect.*—Petioles are mostly slanting upwards with the leaf blades slanting horizontally.

Bracts:

*Number per inflorescence.*—8 to 10.

*Shape.*—Ovate, nearly flat along the mid-rib; strong curling and waviness at the margins.

*Base.*—Acute to obtuse.

*Apex.*—Acuminate.

*Lobes.*—Nearly no lobes.

*Size.*—Length: 7.5 cm to 8.5 cm. Diameter. 5.5 cm to 6.5 cm.

*Texture.*—Strong rugosity.

*Color.*—Upper surface: RHS 46A (deep-red) in the middle; RHS 46B and somewhat brighter near the margins. Lower surface: Often bi-colored, with RHS 54B (dull deep-pink) in the middle; RHS 46B to RHS 46C (bright-red) at the margins. The surface of bracts emerging from the stem under the ring of inflorescence, in the middle part, is usually RHS 137D (greenish), even though the upper surface is completely red.

*Vein color.*—Upper surface: RHS 46A (deep-red) in the middle; RHS 46B and somewhat brighter near the margins. Lower surface: RHS 47A (reddish) or lighter.

*Petiole.*—Length: 0.5 cm to 1.0 cm. Color: Upper surface: RHS 53A (dark-red). Lower surface: Near RHS 47D (pink).

Inflorescence:

*Blooming habit.*—Beginning under natural short-day conditions in the Fall Botanically (cyathia open): Mid-December or later Commercially (bracts colored, marketable): Early December.

*Inflorescence type.*—Small to medium-side with the surrounding curled bracts mostly horizontally directed; in the center a tight cyme with small cyathia.

*Average number of inflorescences.*—5.8.

*Lastingness of inflorescence on the plant.*—About 4 to 6 weeks with no dropping of bracts.

*Diameter.*—16 cm to 21 cm.

*Height.*—4.5 cm.

Cyme:

*Cyme diameter.*—1.5 cm to 2.0 cm.

*Cyathia number.*—7 to 10 borne in a tight cluster.

*Cyathium.*—Shape: Ovate. Diameter: 0.4 cm to 0.5 cm. Length: 0.6 cm to 0.7 cm. Color: Mainly RHS 143C (green), RHS 46B (red) at top.

*Peduncle.*—Color: RHS 143C (light-green). Length: 0.1 cm to 0.2 cm.

*Nectar cups.*—Number: One or two per cyathium. Diameter: 0.3 cm to 0.5 cm. Color: RHS 24A to RHS 32A (orange).

Reproductive organs:

*Stamens.*—Number: 5 to 10 in a cluster. Shape: A narrow strap with two anthers at the upper end. Filaments: Color: RHS 46B (red). Length: 0.2 cm to 0.3 cm. Pollen: None observed.

*Pistil.*—Number: One. Stigma shape: Trifurcate, 6-lobed. Style and stigma color: RHS 46A (dark red).

*Ovary.*—Number of ovules: 3. Shape: Obovate. Length: 0.4 cm. Diameter: 0.3 cm. Color: RHS 143C (light-green).

Fruit and seed set: No seed set observed so far.

Disease and insect resistance: No particular resistance or susceptibility has been observed.

COMPARISON WITH PARENTAL AND COMMERCIAL CULTIVARS

'Carousel Dark Red' differs from the commercial parental poinsettia plant 'Future' (U.S. application Ser. No. 09/590,012—abandoned) by having deeper-red bracts and deeper green foliage than 'Future'. In addition, 'Carousel Dark Red' has a more compact plant habit and mid-season flowering response, while the flowering response of 'Future' is 10 to 12 days later with reference to marketable quality (sufficiently colored bracts).

'Carousel Dark Red' differs from the commercial cultivar 'Fiscor Dark Red' (U.S. Plant Pat. No. 12,723) by having curled bracts, a narrower plant habit, and more upright-directed stems than 'Fiscor Dark Red'.

I claim:

1. A new and distinct cultivar of poinsettia plant as shown and described herein.

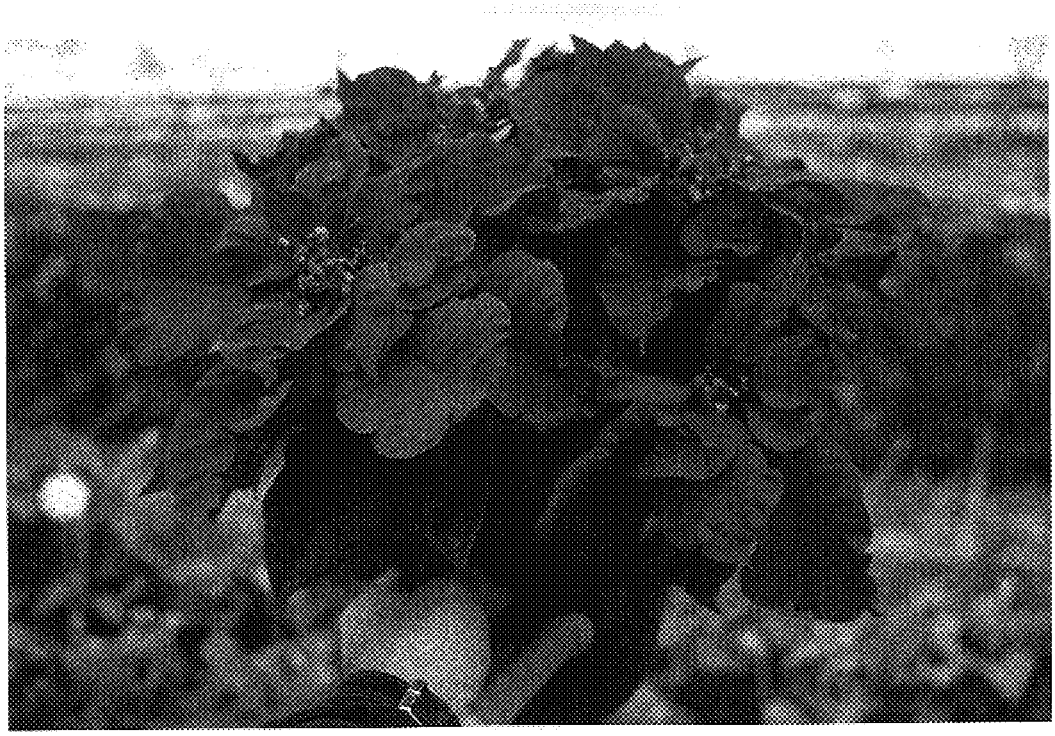

* * * * *